United States Patent [19]

Baker et al.

[11] Patent Number: 4,925,867

[45] Date of Patent: May 15, 1990

[54] HYDROCARBON SUBSTITUTED PYRROLIDINONES, INTERMEDIATES THEREFOR, AND ANTI-CONVULSANT USE THEREOF

[75] Inventors: Raymond Baker, Much Hadham; Paul D. Leeson, Cambridge; Tamara Ludduwahetty, Buckhurst Hill; Brian J. Williams, Great Dunmow, all of England

[73] Assignee: Merck Sharp & Dohme Ltd., Hoddesdon, England

[21] Appl. No.: 414,227

[22] Filed: Sep. 29, 1989

[30] Foreign Application Priority Data

Oct. 7, 1988 [GB] United Kingdom ............... 8823605

[51] Int. Cl.$^5$ ................. C07D 207/273; A61K 31/40
[52] U.S. Cl. ..................... 514/425; 548/542
[58] Field of Search .................. 514/425; 548/542

[56] References Cited

U.S. PATENT DOCUMENTS

| | | | |
|---|---|---|---|
| 3,167,476 | 1/1965 | Bonta | 514/425 |
| 4,585,785 | 4/1986 | Walsh et al. | 514/425 |
| 4,863,953 | 9/1989 | Leeson et al. | 548/542 |

FOREIGN PATENT DOCUMENTS 0115860 5/1988 Japan ..................... 548/542
1041861 2/1963 United Kingdom .

OTHER PUBLICATIONS

Coll. Czech. Chem. Co. . . . , 1959, 24, 1672.
Evans et al., Brain Research, 1978, 148, 536-542.

*Primary Examiner*—David B. Springer
*Attorney, Agent, or Firm*—Manfred Polk; Joseph F. DiPrima

[57] ABSTRACT

Compounds of formula (I) and pharmaceutically acceptable acid addition salts thereof:

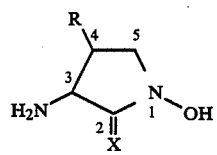

(I)

wherein R represents a hydrocarbon group, X represents oxygen or sulphur, and R and —NH$_2$ are cis; are of use in the treatment and/or prevention of neurodegenerative disorders, and are also useful as anticonvulsant agents and muscle relaxants.

8 Claims, No Drawings

HYDROCARBON SUBSTITUTED PYRROLIDINONES, INTERMEDIATES THEREFOR, AND ANTI-CONVULSANT USE THEREOF

This invention relates to amino pyrrolidinones which are specific antagonists of N-methyl-D-aspartate (NMDA) receptors and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord and head injury and poisoning by exogenous NMDA receptor agonists and neurotoxins. The compounds are also useful as anticonvulsant agents, and muscle relaxants.

The compound 3-amino-1-hydroxypyrrolidin-2-one is disclosed in Coll. Czech. Chem. Comm., 1959, 24, 1672 and its use in the treatment of epilepsy and Parkinson's disease is described in British Patent No. 1,041,861. That compound, known as HA-966, has also been described as being able to antagonise selectively NMDA-induced excitation (Evans et al., Brain Research, 1978, 148, 536–542).

It has now been found that a class of substituted derivatives of HA-966 have dramatically improved NMDA receptor antagonist activity compared with HA-966 itself.

Accordingly, the present invention provides a compound of formula (I) or a pharmaceutically acceptable acid addition salt thereof:

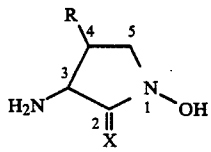

(I)

such that both the substituents R and —NH$_2$ are in a cis-configuration;

wherein R represents a hydrocarbon group and X represents oxygen or sulphur.

Suitable acid addition salts of compound (I) include pharmaceutically acceptable inorganic salts such as sulphate, nitrate, phosphate, borate, hydrochloride and hydrobromide, and pharmaceutically acceptable organic acid addition salts such as acetate, tartrate, maleate, citrate, succinate, benzoate, ascorbate, methanesulphonate, α-ketoglutarate, α-glycerophosphate and glucose-1-phosphate. Preferably the acid addition salt is a hemisuccinate, hydrochloride, α-ketoglutarate, α-glycerophosphate or glucose-1-phosphate, in particular the hydrochloride salt.

The hydrocarbon substituent R may be a straight-chain, branched-chain or cyclic group and may contain up to 18 carbon atoms, suitably up to 13 carbon atoms, and conveniently up to 10 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, heteroaryl and heteroaryl($C_{1-6}$)alkyl.

Suitable alkyl groups include straight-chain and branched-chain alkyl groups containing from 1 to 6 carbon atoms. Typical examples include methyl and ethyl groups, and straight-chain or branched-chain propyl and butyl groups. Particular alkyl groups are methyl, ethyl, iso-propyl and tert-butyl.

Suitable alkenyl groups include straight-chain and branched-chain alkenyl groups containing from 2 to 6 carbon atoms. Typical examples include vinyl and allyl groups.

Suitable alkynyl groups include straight-chain and branched-chain alkynyl groups containing from 2 to 6 carbon atoms. Typical examples include ethynyl and propargyl groups.

Suitable cycloalkyl groups include groups containing from 3 to 7 carbon atoms. A particular cycloalkyl group is cyclopropyl.

Suitable aryl groups include optionally substituted phenyl, naphthyl and tetrahydronaphthyl groups.

The hydrocarbon group R may be substituted by one or more groups selected from $C_{1-6}$ alkyl, phenyl, halogen, trifluoromethyl, hydroxy, $C_{1-6}$ alkoxy, aryloxy, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino, and $C_{2-6}$ alkoxycarbonylamino.

Preferred groups R include methyl, ethyl, iso-propyl, cyclopropyl, terr-butyl, cyclopropylmethyl, phenyl, methylphenyl, methoxyphenyl, halophenyl and benzyl.

To exhibit the superior properties, the compounds of formula (I) have the groups at positions 3 and 4 in a cis configuration, that is both groups are on the same side of the molecule. As both the 3- and 4-positions are chiral centers, the individual isomers comprised by this invention can be represented by structures (IA), the 3-R configuration, and (IB), the 3-S configuration:

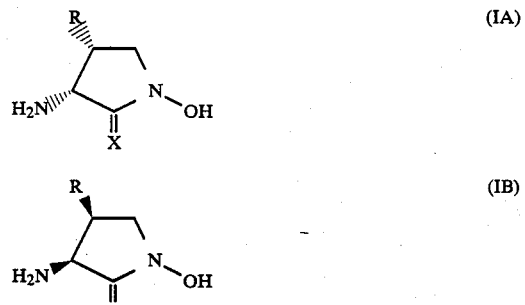

This invention comprises both isomers as well as racemic mixtures thereof. Preferred compounds possess the 3-R stereochemistry as depicted by structure (IA).

Specific compounds of this invention include: cis-3-amino-1-hydroxy-4-methylpyrrolidin-2-one; (3R,4R)-3-amino-1-hydroxy-4-methylpyrrolidin-2-one; cis-3-amino-1-hydroxy-4-ethylpyrrolidin-2-one; and pharmaceutically acceptable acid addition salts thereof.

The invention also provides a pharmaceutical composition comprising a compound of this invention. Preferably the compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of the compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including polymeric acids and mixtures of polymeric acids with such materials as shellac, cetyl alcohol or cellulose acetate.

The liquid forms in which the novel compositions of the present invention may be presented for administration orally or by injection include aqueous solutions, suitably flavoured syrups, aqueous or oil suspensions, and flavoured emulsions with edible oils such as cottonseed oil, sesame oil, coconut oil and peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone and gelatine.

In the treatment of neurodegeneration, a suitable dosage level is about 0.1 to 1000 mg/kg/day, preferably about 0.5 to 500 mg/kg/day and especially about 1 to 100 mg/kg/day. The compounds may be administered on a regimen of 1 to 4 times per day.

The compounds according to the present invention may be prepared by a process which comprises the hydrogenolytic cleavage of a hydrazine derivative of formula (II):

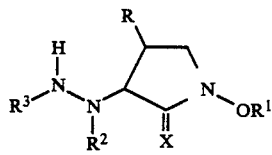

wherein R and X are as defined above; $R^1$ represents hydrogen or a hydroxy-protecting group; and $R^2$ and $R^3$ independently represent hydrogen or an amino-protecting group; followed, where appropriate, by removal of the protecting groups.

The hydrogenolysis reaction is conveniently carried out by treating the compound of formula (II) with hydrogen in the presence of a suitable catalyst, e.g. platinum or palladium.

The compounds of formula (II) may conveniently be prepared by reacting the enolate of a compound of formula (III):

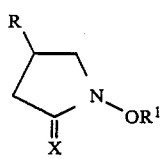

wherein R, $R^1$ and X are as defined above; with a compound of formula (IV):

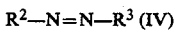

wherein $R^2$ and $R^3$ are as defined above. Preferably $R^2$ and $R^3$ both represent t-butoxycarbonyl.

The reaction is conveniently carried out at a temperature of approximately $-100°$ C. in the presence of a suitable inert organic solvent, e.g. tetrahydrofuran.

The enolate of the compound of formula (III) may conveniently be prepared by treating the appropriate compound of formula (III) with a strong base such as lithium diisopropylamide or potassium hexamethyldisilazide.

An alternative process for the preparation of the compounds according to the invention comprises the deprotection of a compound of formula (V):

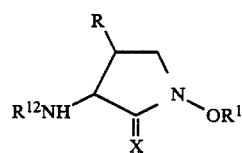

wherein R, $R^1$ and X are as defined above, and $R^{12}$ represents an amino-protecting group.

Examples of hydroxy-protecting groups for the substituent $R^1$ suitably include allyl, alkoxyalkyl, acyloxyalkyl, t-butyl and benzyl. Preferably $R^1$ represents benzyl or t-butyl. Removal of hydroxy protecting groups will be dependent upon the nature of the group concerned, but will in general be effected by conventional means. For example, a benzyl protecting group may conveniently be removed by hydrogenation in the presence of a suitable catalyst, e.g. palladium; and a t-butyl protecting group may conveniently be removed by mild mineral acid hydrolysis.

Suitable examples of amino-protecting groups for the substituents $R^2$, $R^3$ and $R^{12}$ include carboxylic acid groups such as chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p,-methoxyphenylazo)-benzyloxycarbonyl or t-amyloxycarbonyl; acid groups derived from sulphonic acid, e.g. p-toluenesulphonic acid; and other groups such as benzyl, p-methoxybenzyl, trityl, o-nitrophenylsulphenyl or benzylidene.

Preferred amino-protecting groups include t-butoxycarbonyl, benzyloxycarbonyl and p-methoxybenzyl.

The removal of the protecting group present in the resultant compound may be effected by an appropriate procedure depending upon the nature of the protecting group. Typical procedures include hydrogenation in the presence of a palladium catalyst (e.g. palladium carbon or palladium black) for benzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl and trityl groups; treatment with hydrogen bromide in glacial acetic acid or trifluoroacetic acid for benzyloxycarbonyl, p-bromobenzyloxycarbonyl, p-phenylazobenzyloxycarbonyl and t-butoxycarbonyl groups; treatment with hydrochloric acid and/or acetic acid for trityl, t-butoxycarbonyl, formyl and benzylidene groups; and treatment with 2,3-dichloro-5,6-dicyano-1,4-benzoquinone for p-methoxybenzyl groups.

The intermediates of formulae (III) and (V), which may be conveniently represented by the general formula (VI):

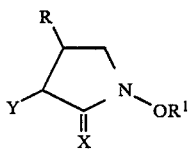
(VI)

wherein R, $R^1$ and X are as defined above, and Y represents hydrogen or $-NHR^{12}$ in which $R^{12}$ is as defined above; are novel compounds and represent a further feature of the present invention.

When the substituent X in the intermediate of formula (VI) above represents sulphur, this compound may be prepared from the corresponding compound of formula (VI) wherein X represents oxygen by treating the latter compound with Lawesson's reagent or phosphorus pentasulphide in a suitable solvent, e.g. pyridine, at ambient or elevated temperatures, suitably at reflux temperature.

The compounds of formula (VI) wherein X represents oxygen may be prepared by cyclisation of a hydroxylamine derivative of formula (VII):

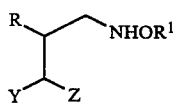
(VII)

wherein R, $R^1$ and Y are as defined above; and Z represents a reactive carboxylate moiety.

Suitable values for the group Z include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group Z represents methoxycarbonyl or ethoxycarbonyl.

The cyclisation is conveniently effected by treatment of the compound of formula (VII) with a base, for example sodium methoxide.

The compounds of formula (VII) may be prepared by reduction of an oximino compound of formula (VIII):

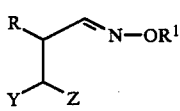
(VIII)

wherein R, $R^1$, Y and Z are as defined above.

A preferred reducing agent for effecting this transformation is sodium cyanoborohydride in a suitable solvent, e.g. an alcoholic solvent such as methanol, in the presence of an acid such as hydrochloric acid, suitably at ambient temperature.

In certain circumstances, the conversion of compound (VIII) to compound (VI) may occur in situ, without the necessity for isolation of the hydroxylamine intermediate of formula (VII).

The compounds of formula (VIII) may be prepared by reaction of an aldehyde of formula (IX):

(IX)

wherein R, Y and Z are as defined above; with a compound of formula $H_2N-OR^1$, in which $R^1$ is as defined above.

The reaction is preferably effected in the presence of a base, e.g. triethylamine, or under mildly acidic conditions, suitably at ambient temperature.

The preparation of a representative compound of formula (IX) wherein Y represents hydrogen is illustrated by the following reaction scheme commencing from ethyl 3-(dimethoxymethyl)crotonate:

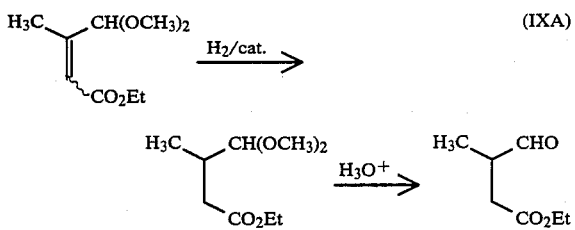
(IXA)

The compounds of formula (IX) wherein Y represents $-NHR^{12}$ may, for example, be prepared by the glycine electrophile methodology described in *Tetrahedron*, 1988, 44, 5403. Thus, treatment of the glycine derivative (X) with bromine or N-bromosuccinimide affords the transient intermediate (XI) which, upon reaction with the activated carbonyl equivalent (XII) followed by a hydrolytic work-up with a mild mineral acid, yields the desired compound of formula (IX):

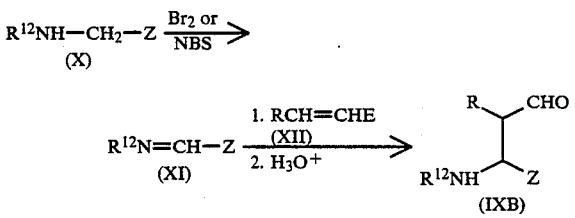
(IXB)

wherein R, $R^{12}$ and Z are as defined above; and E represents a group activating the carbon-carbon double bond for nucleophilic attack.

The compound (XII) is suitably an enamine or a silyl enol ether derivative, in which case the substituent E respectively represents a group of formula $-NR^aR^b$ or $-OSiR^cR^dR^e$ wherein $R^a$ to $R^e$ independently represent, for example, $C_{1-6}$ alkyl; or $R^a$ and $R^b$ together with the intervening nitrogen atom may represent a pyrrolidino, piperidino or morpholino group. In particular, the substituent E may suitably represent a morpholino group; or a trimethylsilyloxy or t-butyldimethylsilyloxy group.

When the substituent E in the compound of formula (XII) represents a group of formula —OSiR$^c$R$^d$R$^e$, the reaction with compound (XI) is preferably effected in the presence of a Lewis acid catalyst, e.g. titanium chloride.

In an alternative method, the compounds of formula (V) above may be prepared by hydrogenation of a compound of formula (XIII):

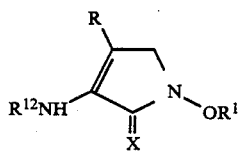

(XIII)

wherein R, R$^1$, R$^{12}$ and X are as defined above.

The reaction is conveniently carried out by treating the compound of formula (XIII) with hydrogen in the presence of a suitable catalyst, e.g. platinum oxide.

The preparation of the intermediates of formula (XIII) wherein R represents oxygen is illustrated by the following synthetic sequence commencing from a corresponding intermediate of formula (III):

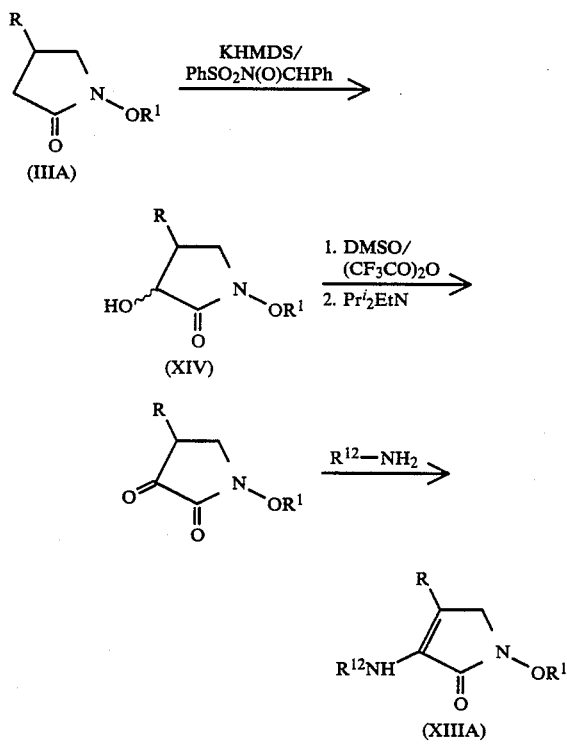

wherein R, R$^1$ and R$^{12}$ are as defined above; and in which KHMDS and DMSO are abbreviations for potassium hexamethyldisilazide and dimethyl sulphoxide respectively.

An alternative method for preparing a typical hydroxylactam intermediate of formula (XIV) above is illustrated by the following reaction scheme:

(XIVA)

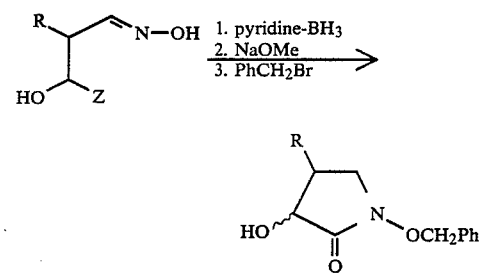

wherein R and Z are as defined above; in particular wherein R represents ethyl and Z represents isopropoxycarbonyl.

The above-described processes for the preparation of the compounds according to the invention may in certain cases produce a mixture of cis and trans isomers. At an appropriate stage, the isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (—)-di-p-toluoyl-d-tartaric acid and/or (+)-di-p-toluoyl-l-tartaric acid followed by fractional crystallization and regeneration of the free base. Alternatively, the novel compounds may be resolved by suitable chemical reaction to form diastereomeric derivatives, followed by chromatographic separation and removal of the chiral auxiliary. For example, a chiral amino-protecting group R$^{12}$ may be employed, which group may be introduced into the molecules concerned at an appropriate stage in the above-described synthetic sequences. A particular chiral amino-protecting group for R$^{12}$ is (R)-1-phenylethyl. Following chromatographic separation of the diastereomers, this group may subsequently be removed, as required, by hydrogenolysis in the presence of a suitable catalyst, e.g. Pearlman's catalyst (palladium hydroxide).

The compounds useful in this invention potently and selectively block responses to NMDA in a brain slice from rat cortex, inhibit glycine binding to the strychnine-insensitive site present on the NMDA receptor, and block the potentiation of NMDA responses by glycine in cultured cortical neurones.

Cortical Slice Studies

The effects of compounds of the invention on responses to NMDA were assessed using the rat cortical slice as described by Wong et al., *Proc. Natl. Acad. Sci. USA*, 1986, 83, 7104. The apparent equilibrium constant (K$_b$) was calculated from the righthand shift in the NMDA concentration-response curve produced by the compound under test. The compounds of accompanying Examples 1 and 2 were tested and the K$_b$ value was found to be below 100 μM in each case.

Inhibition of Glycine Binding

The ability of test compounds to displace $^3$H-glycine binding to the strychnine-insensitive site present on the NMDA receptor of rat forebrain membranes was determined by the method of Donald et al., *Proceedings of*

*The British Pharmacological Society*, University of Nottingham, Sept. 1988, Abstract P122. The concentration of the compounds of the accompanying Examples required to displace 50% of the specific binding ($IC_{50}$) was found to be <20 μM in each case.

Whole-cell Patch-clamp Studies

The ability of test compounds to block the potentiation of NMDA responses by glycine in cultured cortical neurones was measured using patch-clamp techniques as described by Foster and Kemp, *J. Neurosci.*, 1989, 9, 2191. The compounds of the accompanying Examples were tested and were active at concentrations below 20 μM in each case.

EXAMPLE 1 cis-3-Amino-1-hydroxy-4-methylpyrrolidin-2-one

Step A

Ethyl 3-formylbutyrate

A solution of ethyl 3-(dimethoxymethyl)-crotonate (73 g) in ethyl acetate (200 ml) was hydrogenated at 50 psi for 3 h in the presence of 10% palladium on charcoal (7 g). The solution was filtered, evaporated, and the residual oil treated with 0.25 M hydrogen chloride in 75% aqueous methanol for 2 h. To the reaction mixture was added ethyl acetate (300 ml) and water (150 ml). The organic phase was successively washed with sat. sodium bicarbonate solution (3×150 ml), water (100 ml) and dried over magnesium sulfate. The solution was concentrated in vacuo and the residual oil purified by chromatography on silica gel eluting with ethyl acetate-hexane (1:9) to give ethyl 3-formylbutyrate (26.5 g, 48%).

Step B

1-Benzyloxy-4-methylpyrrolidin-2-one

To a solution of ethyl 3-formylbutyrate (25.3 g) in methanol (200 ml) was added triethylamine (30 ml) and 0-benzylhydroxylamine hydrochloride (34 g). After 10 minutes the solvent was removed by evaporation. The residue was dissolved in hexane, the solution was filtered and evaporated to give crude ethyl 3-formylbutyrate 0-benzyloxime. This crude oxime and sodium cyanoborohydride (18 g) were dissolved in methanol (200 ml) and the solution acidified to PH 3-4 (methyl orange indicator) by addition of 2M-hydrochloric acid. After 40 minutes the solution was diluted with water (1L) and basified by addition of 1N sodium hydroxide. The product was extracted into ethyl acetate and the solution dried over magnesium sulfate. The solvent was removed by evaporation and the resultant crude 0-benzylhydroxylamine was dissolved in ethanol (200 ml) and then sodium methoxide (1.2 g) was added. After 2 h the solvent was removed by evaporation and water (1L) added. The product was extracted into ethyl acetate which was dried over magnesium sulfate. Chromatography on silica gel using ethyl acetate/hexane (60:40) as eluent gave 1-benzyloxy-4-methylpyrrolid-2-one (33.2 g, 85%) as a clear oil. $^1$H NMR (250 MHz, CDCl$_3$)δ7.46–7.36 (5H; m; phenyl), 5.01 (1H; d, $J_{gem}$=11.1 Hz; —CH$_A$H$_B$—O), 4.95 (1H; d, $J_{gem}$=11.1 Hz; —CH$_A$H$_B$—O), 3.36 (1H; t, J=8.02 Hz; —CH$_A$H$_B$—N), 2.86 (1H; dd, $J_{gem}$=8.01 Hz, J=8.38 Hz; CH$_A$H$_B$—N), 2.49 (1H; dd, J=16.6 Hz, J=8.64Hz; CO-CH$_A$H$_B$), 2.38–2.17 (1H; m; CH$_3$—CH), 1.92 (1H; dd, $J_{gem}$=16.5 Hz, JJ=6.44 Hz: COCH$_A$H$_B$), 1.03 (3H; d, J=6.8 Hz; CH$_3$—CH).

Step C cis-3-Hydrazino-1-benzyloxy-4-methylpyrrolidin-2-one

1-Benzyloxy-4-methylpyrrolidin-2-one (0.5 g) and di-t-butylazodicarboxylate (0.8 g) were dissolved in anhydrous tetrahydrofuran (5 ml) and the solution cooled with stirring to −100° C. under nitrogen. Potassium hexamethyldisilazide (0.5M in toluene, 5.76 ml) was added dropwise over 20 minutes. The solution was kept at −100° C. for 30 minutes, then at −80° C. for 30 minutes. then recooled to −100° C. and quenched by addition of glacial acetic acid (0.250 ml). The reaction mixture was warmed to ambient temperature and partitioned between ethyl acetate and aqueous citric acid (5%). The organic phase was washed successively with water and brine and dried over magnesium sulfate. The solvent was evaporated and the residue chromatographed on silica gel, eluting with ethyl acetate/hexane (3:7, then 1:1) to give a 1:6 mixture to the cis-and trans-isomers respectively of 3-N,N'-di-t-butoxycarbonylhydrazino-1-benzyloxy-4-methylpyrrolidin-2-one (0.387 g). The isomers were separated by preparative high performance liquid chromatography on a Waters Prep 3000 instrument fitted with a deltapak reverse phase preparative column eluting isocratically with acetonitrile:water:trifluoroacetic acid (45:55:0.1). The cis-3-N,N'-di-t-butoxycarbonyl-hydrazino-1-benzyloxy-4-methylpyrrolidin-2-one so obtained (69 mg) was treated with anhydrous trifluoroacetic acid (5 ml) for 30 minutes. The solvent was removed by evaporation to give cis-3-hydrazino-1-benzyloxy-4-methylpyrrolidin-2-one. $^1$H NMR (250 MHz, CDCl$_3$)δ7.37 (5H; broad s; phenyl), 4.93 (2H; s; benzyl CH$_2$), 3.9 (1H; broad d; CH—CO), 3.4 (1H; dd; CH$_A$H$_B$N), 2.92 (1H; dd; CH$_A$H$_B$N, 2.61 (1H; m; CHCH$_3$), 0.92 (3H; d, J=6.97 Hz; CHCH$_3$). m/e (CI$^+$) 236 (M+H); (EI) 235 (M$^+$).

Step D cis-3-Amino-1-hydroxy-4-methylpyrrolidin-2-one

The hydrazine from step C (69 mg) was dissolved in ethanol (20 ml) and glacial acetic acid (5 ml) and the solution was hydrogenated at 50 psi for 2 h in the presence of palladium black (50 mg). The solution was filtered and further hydrogenated in the presence of platinum oxide (50 mg) at 50 psi for 1.5 h. The solution was filtered and the solvent evaporated to dryness. The residue was dissolved in water (10 ml) and applied to a column containing Dowex 50W-X8 (100–200 mesh, 2×2cm, H$^+$ form). After washing the resin with water (3×15 ml) the product was eluted with dilute aqueous ammonia solution. The fractions containing the product were freeze dried to give cis-3-amino-1-hydroxy-4-methylpyrrolidin-2-one (9.4 mg). $^1$H NMR (250 MHz, D$_2$O) δ3.91 (1H; d, J=8.09 Hz; CO—CH—N), 3.78 (1H; dd, $J_{gem}$=10.0 Hz, J=7.00 Hz; CHHD AH$_B$N), 3.23 (1H; dd, $J_{gem}$=10.1 Hz, J=3.0 Hz; CH$_A$H$_B$N ), 2.79–2.69 (1H; m; CHCH$_3$), 1.10 (3H; d, J=7.22 Hz, CH$_3$). Irradiation of the signal at 2.79ppm gave an NOE to the signals at 3.91 and 3.78, confirming the cis geometry. (m/e: theory, 130.0742; found, 130.0749).

EXAMPLE 2

(3R,4R)-3-Amino-1-hydroxy-4-methylpyrrolidin-2-one

Step A

1-Benzyloxy-3-hydroxy-4-methylpyrrolidin-2one

To a solution of 1-benzyloxy-4-methylpyrrolidin-2-one (53.8 g) and 2-(phenylsulfonyl)-3-phenyloxaziridine (F. A. Davis and O. D. Stringer, J. Org. Chem. (1982), 47, 1774) (72.5 g) in THF (550 ml) at $-100°$ C. was added a 15% solution of hexamethyldisilazide in toluene (525 ml) over 1.5h so that the internal temperature did not rise above $-90°$ C. After the solution was stirred at $-100°$ C. for 30 min glacial acetic acid (50 ml) was added and the solvent removed in vacuo. Methanol (300 ml) and Dowex 50W-X8 ($H^+$ form, 150 g) were added, the solution filtered and the filtrate evaporated to dryness by azeotroping with toluene. The residue was chromatographed on silica gel (250–400 Mesh) eluting with ethyl acetate/hexane (1:1) followed by ethyl acetate alone. The fractions containing the desired product were evaporated, to give a mixture of cis and trans isomers of 1-benzyloxy-3-hydroxy-4-methylpyrrolidin-2-one (29.4 g, 51%) as a crystalline solid. $^1$H NMR (360MHz, $CDCl_3$)$\delta$7.4 (10H, m, phenyl, cis+trans), 5.0 (4H, ss, benzyl, cis+trans), 4.2 (1H, d, J=7.3 Hz, $\alpha C\underline{H}$), 3.8 (1H, d, J=8.4z, $\alpha C\underline{H}$), 3.3 (1H, dd, $J_{gem}$=8.8 Hz, J=6.5 Hz, $C\underline{H}_AH_BN$), 3.2 (1H, t, J=8.4 Hz, $CH_A\underline{H}_BN$), 2.9 (1H, dd, $J_{gem}$=8.7, J=3.0)Hz, $C\underline{H}_AH_BN$), 2.8 (1H, t, J=8.4 Hz, $CH_A\underline{H}_BN$), 2.5 (1H, broad m, $CH_3C\underline{H}$+O$\underline{H}$), 2.1 (1H, m, $CH_3C\underline{H}$), 1.1 (3H, d, J=6.7 Hz, $C\underline{H}_eCH$), 0.97 (3H, d=7.2 Hz, $C\underline{H}_3CH$).

The purified trans isomer was obtained by recrystallization from diethyl ether, mp 112°–113° C.

Step B

1-Benzyloxy-4-methylpyrrolidin-2,3,-dione

Trifluoroacetic anhydride (30 ml, 44 g, 212 mmol) in dry dichloromethane (100 ml) was added dropwise over 15 min to a stirred solution of dimethylsulphoxide (16 ml, 17.6 g, 259 mmol) in dry dichloromethane (500 ml) at $-78°$ C. under nitrogen. After a further 10 min 1-benzyloxy-3-hydroxy-4-methylpyrrolidin-2-one (10 g, 45 mmol) in dichloromethane (80 ml) was added via cannula to the cloudy solution. After 30 min diisopropylethylamine (56 ml, 42 g, 330 mmol) was added dropwise over 5 min, and the reaction stirred for a further 35 min at $-78°$ C. before being quenched at that temperature by the addition of methanol (20 ml). The mixture was then warmed to 0° C., washed with water (300 ml), and the water back extracted twice with dichloromethane. The combined organic layers were washed with brine, the brine extracted with dichloromethane, and the combined dichloromethane layers dried ($Mg_2SO_4$). After evaporation the product was purified by flash chromatography, eluting with dichloromethane: methanol (98:2 v/v) to give 1-benzyloxy-4-methylpyrrolidin-2,3-dione (7.8 g, 78%) as a white solid. In $CDCl_3$ solution the ketone exists in its enol tautomeric form. $^1$H NMR (360 MHz, $CDCl_3$) $\delta$7.3–7.5 (5 H, m, Ph), 5.01 (2 H, s, $OCH_2$), 3.61 (2 H, q, J=0.9 Hz, $NCH_2$), 1.81 (3 H, t, J=0.9 Hz, $CH_3$), m/z (CI, isobutane) 220 ($M^+$+H).

Step C (R)-1-Benzyloxy-4-methyl-2-oxo-3-(1-phenylethylamino)-2,5-dihydropyrrole R-(+)-$\alpha$-methylbenzylamine was purified by crystallization from methanol of its D-(–)-tartrate salt, recrystallization from aqueous methanol and liberation of the free amine by extraction with ether from an aqueous sodium hydroxide solution. After evaporation of the ether the amine was used without distillation. It had an e.e. of >99.99% (chiral HPLC).

1-Benzyloxy-4-methylpyrrolidin-2,3-dione (7.8 g, 35.6 mmol) and R-(+)-$\alpha$-methylbenzylamine (8 ml, 7.5 g, 62 mmol) were stirred in methanol (250 ml) at 55° C. for 14 h then refluxed for 4 h. The mixture was then cooled, evaporated and purified by flash chromatography, eluting with hexanes: ethyl acetate (4:1 v/v) to give (R)-1-benzyloxy-4-methyl-2-oxo-3-(1-phenylethylamino)-2,5-dihydropyrrole (8.95 g, 78%) as a slightly yellow oil. $^1$H NMR (360 MHz, $CDCl_3$) $\delta$7.2–7.5 (10 H, m, Ph's), 5.00 (2 H, s, $OCH_2$), 4.64 (1 H, q, J=6.8 Hz, NCH), 4.1 (1 H, br s, NH), 3.50 (1H, d, J=16.2 Hz, $NCH_AH_B$), 3.43 (1 H, d, J=16.2 Hz, $NCH_AH_B$), 1.60 (3 H, s, $CH_3CCH_2$), 1.45 (3 H, d, J=6.8 Hz, $CH_3CHPh$), m/z (CI, $NH_3$) 323 ($\underline{M}^+$+H).

Step D (3R,4R)-1-Benzyloxy-4-methyl-3-[(R)-1-phenylethylamino]pyrrolidin-2-one R-1-Benzyloxy-4-methyl-2-oxo-3-(1-phenylethylamino)-2,5-dihydro pyrrole (8.95 g, 27.6 mmol) was hydrogenated on platinum (IV) oxide (900 mg) in a mixture of ethyl acetate (300 ml) and acetic acid (30 ml) at atmospheric pressure for 14 h. The mixture was then filtered, evaporated in vacuo, azeotroped with toluene, dissolved in methanol (250 ml), and $K_2CO_3$ (19 g, 137 mmol) and benzyl bromide (3 ml, 4.3g, 25 mmol) added. After stirring for 2 h the mixture was poured into water, extracted three times with ether, and the combined organic layers washed with water and brine, dried ($Mg_2SO_4$). evaporated in vacuo, and purified by flash chromatography, eluting with hexanes:ethyl acetate (5–2:1 v/v) to give a mixture (2:1) of (3R,4R)-1-benzyloxy-4-methyl-3-[(R)-1-phenylethylamino]pyrrolidin-2-one and (3S,4S)-1-benzyloxy-4-methyl-3-[(R)-1-phenylethylamino]pyrrolidin-2-one (7.10 g, 79%) as an oil. The diastereoisomeric amines could be separated on a Waters PrepLC 500. The columns were equilibrated with 0.5% MeOH in $CH_2Cl_2$, then the product loaded, and eluted with 5l of the same mixture then the solvent changed to 0.6% MeOH in $CH_2Cl_2$. Fractions containing the desired product were evaporated in vacuo. Major isomer: $^1$H NMR (360 MHz, $CDCl_3$)$\delta$7.3–7.6 (10 H, m, Ph's), 5.03 (1 H, d, J=11 Hz, $OCH_AH_B$, 4.99 (1 H, d, J=11 Hz, $OCH_AH_B$), 4.24 (1 H, q, J=6.5 Hz, NCHPh), 3.27 (1 H, dd, J=2.7 and 8.6 Hz, $NCH_AH_B$), 3.20 (1 H, d, J=7.4 Hz, NCHCO), 2.80 (1 H, dd, J=0.5 and 8.6 Hz, $NCH_AH_B$), 1.95–2.05 (1 H, m, $CHCH_2$), 1.43 (3 H, d, J=6.5 Hz, $CH_3CHPh$), 0.88 (3 H,d,J =7.0 Hz, $CH_3CHCH_2$), m/z (CI, $NH_3$) 325 ($\underline{M}^+$+H). Minor isomer: $^1$H NMR (360 MHz, $CDCl_3$)$\delta$7.2–7.5 (10 H, m, Ph's), 4.97 (1 H, d, J=11.0 Hz, $OCH_AH_B$), 4.92 (1 H, d, J=11.0 Hz, $OCH_AH_B$), 3.75 (1 H, q, J=6.7 Hz, NCHPh), 3.27 (1 H, dd, J=5.9 and 8.6 Hz, $NCH_AH_B$), 3.15 (1 H, d, J=7.3 Hz, NCHCO), 2.80 (1 H, dd, J=0.7 and 8.6 Hz, $NCH_AH_B$), 2.3–2.4 (1 H, m, $CHCH_2$), 1.38

(3 H, d, J=6.7 Hz, CH$_3$CHPh), 0.95 (3 H, d, J=7.0 Hz, CH$_3$CHCH$_2$), m/z (CI, NH$_3$) 325 (M+H).

Step E (3R,4R) 3-Amino-1-hydroxy-4-methylpyrrolidin-2-one, (−) tartrate salt (3R,4R)-1-Benzyloxy-4-methyl-3-[(R)-1-phenylethylamino]pyrrolidin-2-one (6.4 g. 19.7 mmol) was hydrogenolysed on Pearlman's catalyst (1.6 g) in methanol (100 ml) and acetic acid (2 ml) for 2 h at 50 psi. After filtration and evaporation, the residue was dissolved in water and applied to a column containing DOWEX 50W-X8 (100–200 mesh, 4×4 cm, H+ form). After washing the resin with water (150 ml) the product was eluted with dilute aqueous ammonia. The fractions containing the product were freeze dried to give (3R,4R)-3-amino-1-hydroxy-4-methylpyrrolidin-2-one (2.3 g, 90%) as a white foam. [α]$_D$= +16.3° (c=0.48, MeOH). The $^1$H NMR of this product was identical to that of the racemate. To the foam was added D-(−)-tartaric acid (1.33 g), the solids dissolved in water, and freeze dried to give (3R,4R)-3-amino-1-hydroxy-4-methylpyrrolidin-2-one, (−)tartrate salt (3.91 g). $^1$H NMR (360 MHz, D$_2$O) 4.36 (1 H, s, CHOH), 4.24 (1 H, d, J=8.4 Hz, CHN), 3.90 H(1H, dd, J=6.6 and 9.5 Hz, NCH$_A$H$_B$), 3.34 (1 H, dd, J=2.2 and 9.5 Hz, NCH$_A$H$_B$), 2.8–3.0 (1 H, m, CHCH$_3$), 1.74 (3 H, d, J=7.1 Hz, CH$_3$), m/z (CI, NH$_3$) 131 (M+ +H) (Found: C, 38.09; H, 6.65; N, 12.65. C$_7$H$_{13}$N$_2$O$_5$+0.9 H$_2$O requires C, 37.97; H, 6.73, N, 12.65). Analysis by HPLC on a chiral stationary phase found enantiomeric purity of 99.66%.

EXAMPLE 3

Cis-3-Amino-1-hydroxy-4-ethylpyrrolidin-2-one

Step A

Isopropyl 2-hydroxy-3-hydroxyliminomethylpentanoate n-Butyllithium (74 ml of a 1.6M solution in hexanes, 118 mmol) was added dropwise over 5 min to a solution of butyraldehyde oxime (5.12 g, 58.8 mmol) in THF (150 ml) at −78° C. The thick white suspension was warmed to room temperature for 30 min until the solid had dissolved to give a yellow solution. The solution was then cooled to −78° C. and cannulated into a stirred solution of isopropyl glyoxylate (6.8 g, 58.6 mmol) in THF (100 ml) at −78° C. After a further 30 min, the mixture was warmed to room temperature. poured into brine, and extracted with ether (3×150 ml). The combined organic layers were dried (MgSO$_4$). evaporated in vacuo, and purified by flash chromatography, eluting with dichloromethane: methanol (20:1 v/v) to give a mixture of two isomers (3:2 by NMR) of isopropyl 2-hydroxy- 3-hydroxyliminomethylpentanoate (2.89 g, 25%) as an oil. $^1$H NMR (250 MHz, CDCl$_3$)δ6.72 (d, J=7.6 Hz, CHN, major isomer), 6.68 (d, J=7.6 Hz, CHN, minor isomer), 5.0–5.1 (1 H, m, CHCH$_3$), 4.34 (d, J=4.0 Hz, CHCO, major isomer), 4.24 (d, J=3.1 Hz, minor isomer), 3.4–3.5 (1 H, m, CHH$_2$), 1.5–2.0 (2 H, m, CH$_2$), 1.2–1.3 [6 H, m, CH(CH$_3$)], 0.8–1.0 (3 H, m, CH$_3$CH$_2$), m/z (CI,NH$_3$) 204 (M+H).

Step B 1-benzyloxy-4-ethyl-3-hydroxypyrrolidin-2-one

10% Aqueous hydrochloric acid (30 ml) was added dropwise over 5 min to a stirred solution of 2-hydroxyliminomethylpentanoate (1.74 g, 8.57 mmol) and pyridine - borane complex (3 ml, 2.7 g, 29 mmol) in ethanol (15 ml) at 0° C. After the addition was complete the mixture was stirred at room temperature for 30 min. basified to pH9 with solid sodium carbonate and extracted with dichloromethane (3×25 ml). The combined organic layers were washed with brine, dried (MgSO$_4$). evaporated in vacuo, the residue dissolved in methanol (20 ml), and sodium methoxide (0.56 g. 10.4 mmol) added. The solution was then refluxed for 2 h, cooled to room temperature. and benzyl bromide (1.5 ml, 2.16 g, 12.6 mmol) added. After stirring for 16 h sodium methoxide (0.5 g) was added, and the mixture stirred for a further 30 min before being poured into water, and extracted with ether (3×30 ml). The combined organic layers were washed with water and brine, dried (MgSO$_4$), evaporated in vacuo, and purified by flash chromatography. eluting with dichloromethane : methanol (96:4 v/v) to give 1-benzyloxy-4-ethyl-3-hydroxypyrrolidin-2-one as a mixture of isomers (2:1 by NMR) (1.10 g, 55%) as an oil. $^1$H NMR (360 MHz, CDCl$_3$) Major isomer: δ7.4–7.5 (5 H, m, Ph), 5.03 (1 H, d, J=11.0 Hz, OCH$_A$H$_B$), 4.98 (1 H, d, J=11.0 Hz, OCH$_A$H$_A$), 3.91 (1 H, d, J=8.2 Hz, CHOH), 3.31 (1 H, t, J=8.5 Hz, NCH$_A$H$_B$), 2.87 (1 H, t, J=8.5 Hz, NCH$_A$H$_B$), 2.0–2.1 (1 H, m, CHCH$_2$), 1.7–1.8 and 1.3–1.4 (2 H, m, CH$_2$CH$_3$), 0.91 (3 H, t, J=7.44 Hz, CH$_3$). Minor isomer δ7.4–7.5 (5 H, m, Ph), 5.00 (2 H, s, OCH$_2$), 4.24 (1 H, d, J=7.3 Hz, CHOH), 3.28 (1 H, dd, J=6.8 and 8.8 Hz, NCH$_A$H$_B$), 3.06 (1H, dd, J=4.7 and 8.8 Hz, NCH$_A$H$_B$), 2.1–2.2 (1 H, m, CHCH$_2$), 1.7–1.8 and 1.2–1.3 (2 H, m, CH$_2$CH$_3$), 0.84 (3 H, t, J=7.4 Hz, CH$_3$), m/z (CI, NH$_3$) 236 (M+ +H).

Step C

1-Benzyloxy-4-ethyl-3-(4-methoxybenzylamino)-2-oxo-2,5-dihydropyrrole

Trifluoroacetic anhydride (1.8 ml, 2.6 g, 12.7 mmol) was added dropwise to a solution of dimethylsulphoxide (1 ml, 1.1 g, 16.2 mmol) in dichloromethane (40 ml) at −78° C. After 10 min 1-Benzyloxy-4-ethyl-3-hydroxypyrrolidin-2-one (0.94 g, 4 mmol) in dichloromethane (8 ml) was added, the mixture stirred for 30 min, then ethyldiisopropylamine (4.5 ml, 3.4 g, 26.3 mmol) added. After 45 min methanol (1 ml) was added and the solution brought to room temperature. Water was added and the mixture extracted with ether (3×75 ml). The combined organic layers were washed with brine, dried (MgSO$_4$), evaporated in vacuo, and the residue dissolved in methanol (10 ml). 4-Methoxybenzylamine (1.1 ml) was added and the solution kept at room temperature overnight. The solvent was then removed in vacuo, and the product purified by flash chromatography, eluting with light petroleum:ethyl acetate (5:2 v/v) to give 1-benzyloxy-4-ethyl-3-(4-methoxybenzylamino)-2-oxo-2,5-dihydropyrrole as an oil (0.74 g, 55%). $^1$H NMR (250 MHz, CDCl$_3$) δ7.4–7.5 (5 H, m, ph), 7.22 (2 H, d, J=9 Hz, MeOCCH), 6.85 (2 H, d, J=9 Hz, MeCCHCH), 5.02 (2 H, s, OCH$_2$), 4.32 (2 H, s, CH$_2$NH), 3.78 (3 H, s, OMe), 3.60 (2 H, s, CH$_2$NO), 2.22 (2 H, q, J=7 Hz, CH$_2$CH$_3$), 0.93 (3 H, t, J=7 Hz, CH$_3$), m/z 353 (M+ +H).

Step D cis-1-Benzyloxy 4-ethyl-3-(4-methoxybenzylamino)pyrrolidin-2-one

1-Benzyloxy-4-ethyl-3-(4-methoxybenzylamino)-2-oxo-2,5-dihydropyrrole (72 mg, 205 μmol) was hydrogenated on platinum (IV) oxide (9.6 mg) in ethyl acetate (10 ml) and acetic acid (100 μl) at atmospheric pressure for 20 h. The mixture was filtered, washed with sodium hydrogen carbonate solution and brine, dried (MgSO$_4$), and evaporated in bacuo to give cis-1-benzyloxy-4-ethyl-3-(4-methoxybenzylamino)pyrrolidin-2-one (72 mg, 100%) as an oil. $^1$H NMR (250 MHz, CDCl$_3$) δ7.3–7.5 (5 H, m, Ph), 7.26 (2 H, d, J=9 Hz, MeOCCH), 6.84 (2 H, d, J=9 Hz MeOCCHCH), 4.98 (2 H, s, OCH$_2$), 3.80 (2 H, s, CH$_2$NH), 3.78 (3 H, s, OMe), 3.30 (1 H, d, J=8.5 Hz, NCH̄), 3.25 (1 H, dd, J=6 and 10 Hz, CH$_A$H$_B$NO), 2.95 (1 H, dd, J=3 and 10 Hz, CH̄$_A$H$_B$NO), 2.0–2.1 (1 H, m, CHCH$_2$), 1.5–1.6 and 1.0–1.1 (2 H, m, CH$_2$CH$_3$), 0.74 (3 H, t, J=7.5 Hz, CH$_3$), m/z (CI, NH$_3$) 249 (M−MeOC$_6$H$_4$+H).

Step E cis-3-Amino-1-hydroxy-4-ethylpyrrolidin-2-one

Dichlorodicyanobenzoquinone (125 mg, 550 μmol) was added to a stirred solution of cis-1-benzyloxy-4-ethyl-3-(4-methoxybenzylamino) pyrrolidin-2-one (190 mg, 458 μmol) in dichloromethane (20 ml) and water (1 ml). After 90 min the mixture was evaporated, dissolved in dilute hydrochloric acid, and applied to a column containing DOWEX 50W-X8 (100–200 mesh, 2×2 cm, H+ form). After washing the column with water (100 ml), the product was eluted with dilute aqueous ammonia. Fractions containing the product were evaporated in vacuo, then purified by flash chromatography, eluting with dichloromethane: methanol (95:5 v/v). The resulting oil (62 mg) was hydrogenated on palladium black (30 mg) in ethanol (20 ml) and acetic acid (200 μl) at 50 p.s.i. for 2 h. After filtration and evaporation, the residue was dissolved in water and applied to a column containing DOWEX 50W-X8 (100–200 mesh, 2×2 cm, H+ form) After washing the column with water (50 ml), the product was eluted with dilute aqueous ammonia. Fractions containing the desired product were freeze dried to give cis-3-amino-1-hydroxy-4-ethylpyrrolidin- 2-one (29.1 mg, 45%) as a white powder. $^1$H NMR (360 MHZ, D$_2$O) δ3.82 (1 H, d, J=8.0 Hz, CHN), 3.69 (1 H, dd, J=7.3 and 10.0 Hz, NCH$_A$H$_B$), 3.38 (1 H, dd, J=4.8 and 10 0 Hz, NCH$_A$H$_B$), 2.45–2.55 (1 H, m, CHCH$_2$), 1.5–1.6 and 1.3–1.4 (2 H, m, CH$_2$CH$_3$), 0.96 (3 H, t, J=7.3 Hz, CH$_3$), m/z (CI, NH$_3$) 145 (M++H).

EXAMPLE 4

Tablet Preparation

Tablets containing 1.0, 2.0, 25.0, 26.0, 50.0 and 100.0 mg, respectively, of the following compounds are prepared as illustrated below:
Cis-3-amino-1-hydroxy-4-methylpyrrolidin-2-one.
(3R, 4R)-3-amino-1-hydroxy-4-methylpyrrolidin-2-one.
Cis-3-amino-1-hydroxy-4-ethylpyrrolidin-2-one.

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amoung-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of active ingredient per tablet.

What is claimed is:

1. A compound of formula (I) or a pharmaceutically acceptable acid addition salt thereof:

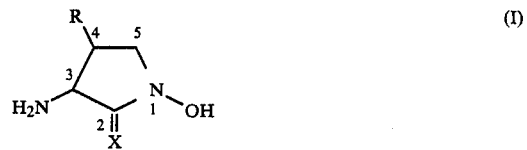

such that both the substituents R and —NH$_2$ are in a cis-configuration;
wherein R represents a hydrocarbon group or aryl optionally substituted with one or more halogen or C$_1$–C$_6$ alkoxy groups and X represents oxygen or sulphur.

2. A compound according to claim 1 wherein R is selected from the group consisting of methyl, ethyl, isopropyl, cyclopropyl, t-butyl, cyclopropylmethyl, phenyl, methylphenyl, methoxyphenyl, halophenyl and benzyl.

3. A compound according to claim 1 wherein the stereochemical configuration at the 3-position is (R).

4. A compound selected from: cis-3-amino-1-hydroxy-4-methylpyrrolidin-2-one; (3R,4R)-3-amino-1-hydroxy-4-methylpyrrolidin-2-one; cis-3-amino-1-hydroxy-4-ethylpyrrolidin-2-one; and pharmaceutically acceptable acid addition salts thereof.

5. A pharmaceutical composition comprising an effective amount of a compound according to claim 1 in association with a non-toxic pharmaceutically acceptable carrier or excipient.

6. A method for the treatment and/or prevention of neurodegenerative disorders, which method comprises administering to a patient in need of such treatment an effective amount of a compound according to claim 1.

7. A method for the treatment and/or prevention of convulsions, which method comprises administering to a patient in need of such treatment an effective amount of a compound according to claim 1.

8. A compound of formula (VI):

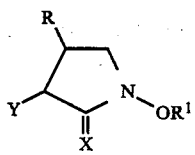 (VI)

wherein R and X are as defined in claim 1; $R^1$ represents hydrogen or a hydroxy-protecting group; and Y represents hydrogen or $-NHR^{12}$, in which $R^{12}$ represents an amino-protecting group.

* * * * *

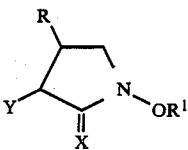 (VI)

wherein R and X are as defined in claim 1; $R^1$ represents hydrogen or a hydroxy-protecting group; and Y represents hydrogen or $-NHR^{12}$, in which $R^{12}$ represents an amino-protecting group.

* * * * *